United States Patent [19]
Flaherty

[11] Patent Number: 5,450,745
[45] Date of Patent: Sep. 19, 1995

[54] EDGE STRENGTH TESTER

[76] Inventor: Frank Flaherty, 12 Falmouth Landing Rd., E. Falmouth, Mass. 02536

[21] Appl. No.: 282,304

[22] Filed: Jul. 29, 1994

[51] Int. Cl.⁶ .............................................. G01N 19/00
[52] U.S. Cl. ............................................. 73/82; 73/83; 73/104
[58] Field of Search ...................... 73/81–83, 73/104

[56] References Cited

U.S. PATENT DOCUMENTS

| | | | |
|---|---|---|---|
| 4,111,039 | 9/1978 | Yamawaki et al. | 73/82 |
| 4,671,104 | 6/1987 | Fischer | 73/81 |
| 4,691,559 | 9/1987 | Fischer | 73/81 |
| 4,699,000 | 10/1987 | Lashmore et al. | 73/81 |

FOREIGN PATENT DOCUMENTS 919437 10/1954 Germany ........................... 73/81

Primary Examiner—Robert Raevis
Attorney, Agent, or Firm—Norman B. Rainer

[57] ABSTRACT

A device for testing a specimen for the purpose of ascertaining strength of an edge or hardness of a surface employs a pivoted rocker arm whose two extremities are interactive with voice coils that impart a controlled torque and velocity to the rocker arm. A diamond indenter and a linear variable differential transformer displacement gauge (LVDT) are also attached to the rocker arm. The torque produces a corresponding force on the indenter. A holder positions the specimen opposite the indenter, The degree of indentation produced in the specimen at two different force levels is measured by the LVDT.

7 Claims, 1 Drawing Sheet

EDGE STRENGTH TESTER

BACKGROUND OF THE INVENTION

1. Field of the Invention

This invention relates to test apparatus, and more particularly concerns an improved edge strength tester having an indenting member and means for controlling the velocity and force exerted upon said indenting member.

2. Description of the Prior Art

Cutting implements are in general subject to utilization by virtually every household and industry for the cutting or severing of an indeterminable number of items. In each environ, whether domestic, industrial, or the like, quite obviously the efficiency of the blade or cutting implement is dependent upon a properly sharpened cutting edge.

Various techniques are utilized for creating sharpened cutting edges. Often it is assumed that because an edge has been subjected to a sharpening process, that the proper sharpness has been achieved. However, incorrectly sharpened edges may result from grinding wheel burning, wire edges or burrs, large tip radii, improper hardening, incorrect geometry, and other factors.

In the industrial production of cutting blades, much attention must be given to the particular sharpening technique utilized for each type of blade, and its intended usage. The ability to measure edge strength is accordingly necessary for purposes of optimizing and monitoring production techniques.

Edge strength, a criterion of effective performance characteristics, is related to the blade edge angle and the hardness of the edge material.

Various concepts have been employed in attempts to determine the sharpness of a cutting edge. Such edges may include but are not limited to knife blades, razor blades, surgical scalpels, industrial slitters, chippers, granuletots, etc. For example, U.S. Pat. No. 4,528,843 to Juranitch discloses an edge sharpness tester which includes an elongated body of material into which a properly sharpened edge only will bite when slid lightly therealong at a predetermined angle. However, there is no correlation between test results and strength of the edge or its effectiveness in use.

U.S. Pat. No. 4,178,797 to Kozlowski, Jr, provides a machine for testing the relative sharpness of surgical knife blades wherein the blade is forced into contact with a rotated rod. The blade cuts into the rod more deeply with each turn. The number of turns required to sever the rod determines the relative sharpness of an edge. The Kozlowski tester is not capable of measuring small differences in extremely sharp edges due to its inability to control the velocity at which the test blade approaches the rod, the resultant force exerted by the blade upon the rod, and the frictional force of the rod on the opposite facets of the edge, The Kozlowski tester does not ascertain whether the dullness is a result of a weak edge geometry which crumbles during the test or an initially dull but strong edge. The measured frictional force may not be related to the final use of the edge.

U.S. Pat. No. 3,931,732 to Yon Heirlinger discloses a hand held tool for testing the edge sharpness of non-cutting edges for the purpose of hazard prevention. The device employs a rotatable mandrel carrying a covering of testing material which contacts the edge to be tested.

Various non-contacting test instruments have been disclosed in recent years. For example, U.S. Pat No. 5,196,800 to Graff et al. discloses a non-contacting sharpness tester adapted to measure the sharpness of the edge of a circular slitting knife. This technique involves repeatably placing a capacitance sensor probe symmetrically over the edge at a predetermined distance from a calibrated sharp edge and measuring capacitance to derive a measurement that varies with knife wear. This measures wear from use, not initial sharpness. The Graff device is insensitive to the small tip radius changes of razor blade edges, and gives no indication of the initial condition of the edge prior to use. Accordingly, it cannot be employed as a process correction device.

A testing device which had widespread early usage in industry is based upon the principle of optically measuring the penetration of a restrained blade edge into a standard material under a fixed load, This method indented the edge with a light load of a few grams, pushing a diamond wedge with an included angle of 170 degrees. The large included wedge angle made minimum penetration into the edge so that very small depths could be sampled. The large angle made an elongated indent along the edge which could be measured by a filar eyepiece on a high magnification microscope. This is an expensive and time consuming method for controlling production.

In more recent industrial usage, the depth of the indent is measured directly. A minor load (about one gram or less) is used to locate the edge, and a heavier load (30 grams) deforms the bulk of the edge. If a displacement gauge is placed with the diamond wedge, the difference of penetration can be measured directly. It has been found that this reading gives a direct indication of the blade material hardness, the geometrical angle of the edge and the tip radius. It also correlates well with the optical method.

One of the difficulties of this method is that building vibration, namely seismic effects on the building, cause the readings to increase in an uncontrolled manner, giving an erroneous indication of penetration. This vibration is related to the inertia of the mechanical system holding the diamond wedge. It is particularly important to keep the mass of the members of the instrument to a minimum. These members are the diamond Indenter, the displacement gauge, the force or load-imparting device and the mechanical parts holding them together. In particular, this mass should be less than 50 grams.

Further, the velocity of the diamond wedge approaching the edge must be controlled so that the momentum of the diamond does not transfer sufficient energy so that it exceeds the force of the minimum load. This energy is a function of both the mass of the assembly and its velocity, and both must be minimized to get true readings. It is the purpose of this invention to keep the mass small as well as to incorporate a velocity control which prevents excessive speed.

It is therefore an object of the present invention to provide an edge strength test instrument capable of producing precise, accurate, and repeatable measurements.

It is another object of the present invention to provide a tester of the aforesaid nature having means for controlling the approach velocity of a penetrator element to the blade.

It is yet another object of this invention to provide a tester of the aforesaid nature wherein the mass of the penetrator element and associated components is minimized.

It is a further object of this invention to provide a tester of the aforesaid nature which is adaptable to various blades, quick in operation and capable of providing information useful in remediating the blade-producing process.

These and other beneficial objects and advantages will be apparent from the following description.

SUMMARY OF THE INVENTION

The above and other beneficial objects and advantages are accomplished in accordance with the present invention by a device for measuring the strength of a cutting edge of a blade and measuring the hardness of a surface, said device comprising:

a) an elongated rocker arm extending to first and second extremities, each extremity having opposed front and rear surfaces, said rocker arm supported at its midpoint by pivot means,
  b) a first coil of electrical wire mounted upon said front surface adjacent said first extremity and interactively associated with a stationary first magnet mounted separately from said rocker arm in a manner such that an electrical current fed to said first coil causes said coil to move toward said magnet, thereby imparting torque to said rocker arm,
  c) an assembly consisting of a second coil of electrical wire connected to a threaded rod member orthogonal with respect to the rocker arm at the second extremity and suspended by springs whose other end is mounted to a fixed frame and interactively associated with a stationary second magnet also mounted to the fixed frame in such a manner that a D. C. electrical current causes said second coil and its rod to move towards its second magnet, thereby imparting torque to said rocker arm in a direction opposite to the torque produced at said first extremity,
  d) a rod part of the second coil assembly which is threaded at its extremity protruding through an aperture in the rocker arm and fitted with threaded nut restraining the rocker arm rear surface when the D.C. current of one polarity is applied to the second coil and releasing it when the polarity of the current is reversed,
  e) a diamond wedge orthogonally emergent from the rear surface of said second extremity and positioned to impinge upon a blade whose edge is to be tested,
  f) holding means for adjustably securing said blade in operative juxtaposition with said wedge,
  g) means for supplying time variable D.C. current independently to said coils, and
  h) measuring means for producing a read-out corresponding to the distance of movement of said wedge.

In a preferred embodiment, the measuring means is a linear variable differential transformer displacement gauge having an inner core attached to said rocker arm, and an outer core which is held in a fixed position. Said second coil is preferably mounted upon a post of adjustable length secured to said rocker arm.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
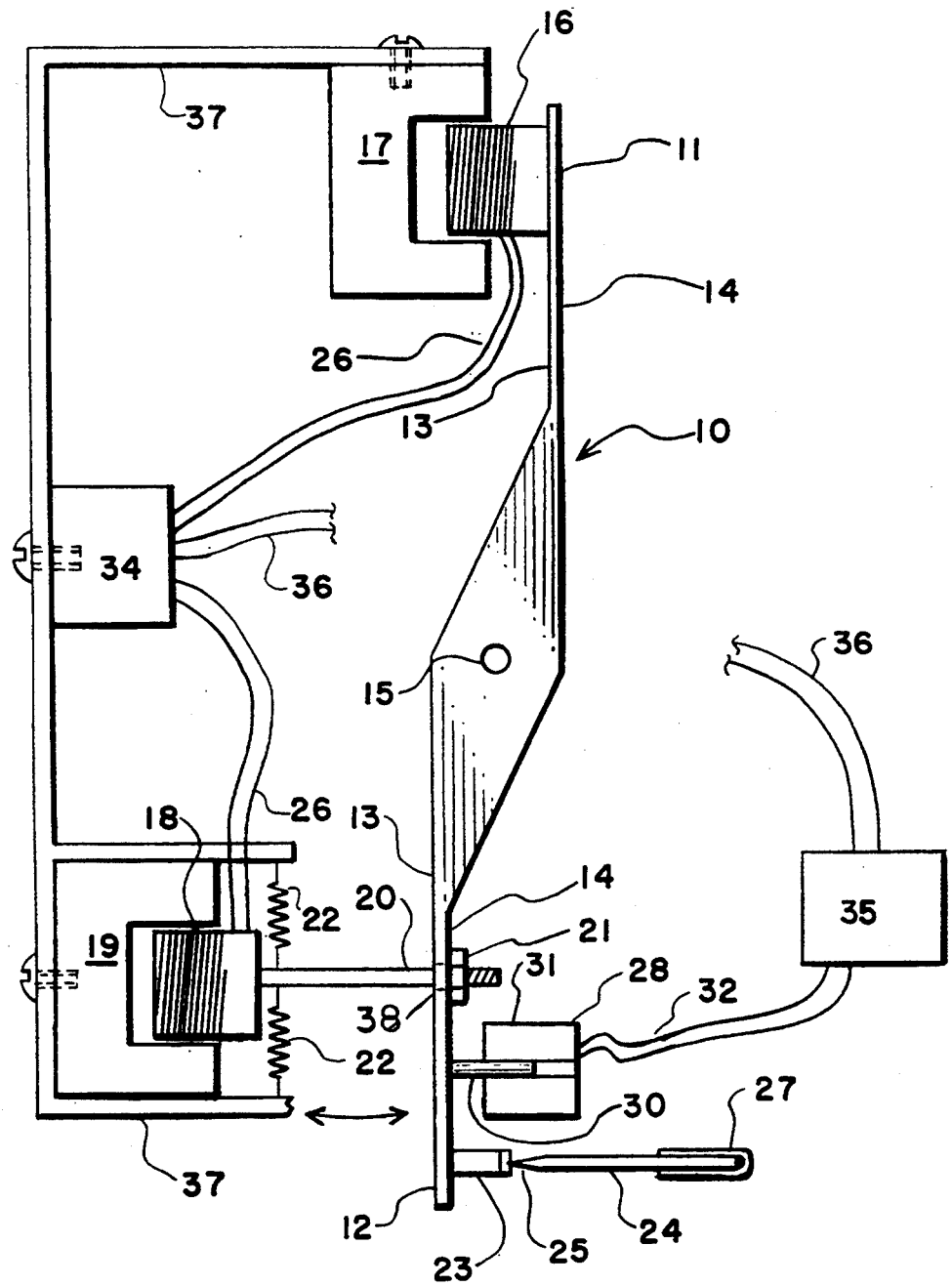
FIG. 1 is a schematic side view of an embodiment of the testing device of the present invention.

Referring to FIG. 1, an embodiment of the testing device of this invention is shown having an elongated rigid rocker arm 10 extending to first and second flat extremity portions 11 and 12 respectively. The extremity portions have opposed front and rear surfaces 13 and 14, respectively. The rocker arm is supported at its mid point by pivot means in the form of a bearing 15, permitting a reciprocating rotative or rocking motion whereby said front and rear surfaces become alternatively leading and trailing surfaces. The rocker arm, which may be of metal or plastic construction, may have an overall length between about 2 and 10 inches. The front and rear surfaces may have widths between about ¼ and 1 ½ inches. It is to be noted that said extremity portions in the illustrated embodiment are not disposed in a straight line but are instead offset with respect to rod 15 in parallel relationship. The spacing between the parallel planes containing the offset extremity portions is between about ⅛ and ¾ inches, the specific value being dependent upon the length and width of the rocker arm.

A first coil of electrical wire 16 is mounted upon the first surface 13 of said first extremity portion 11. Said coil 16 is interactively associated with a first permanent magnet 17 fixedly mounted, as to a surrounding housing 37 shown fragmentarily, separate from the rocker arm. The combination of said coil 16 and magnet 17 constitute a voice coil of the general type employed in loudspeakers. The principle of such interaction is that the force of the moveable coil relative to the magnet is a function of the D.C. electrical current fed to the electrical wire of coil 16. By virtue of the attraction of the coil to the magnet, a torque is produced by said first voice coil upon said first extremity portion. Magnet 17 preferably produces a magnetic field of over 5000 gauss. The coil preferably has an 8 to 12 ohm length of #37 copper wire wrapped in a double layer around an insulator ring about ⅝ inch diameter which fits into the magnet, producing an annular air gap of about 0.015". Wire leads 26 which service the coil are electrically connected to a current source and computer means through wire leads 36.

A second coil of electrical wire 18 is connected to a threaded rod 20 and this combination is suspended on springs free of the rocker arm. Said coil 18 is interactively associated with a second permanent magnet 19 fixedly mounted separate from said rocker arm. The combination of coil 18 and magnet 19 constitutes a second voice coil, as in the case of said first coil and magnet combination. The performance characteristics of the second voice coil may be essentially the same as for the first voice coil. A rod 20 is attached to coil 19 and is positioned to fit through an aperture 38 of about ¼ inch circumference in the rocker arm. A nut 21 is threaded onto the rod 20 and this nut contacts and restrains the rear surface of the rocker arm in the rest position. The extent to which coil 18 is spaced from the rocker arm is controlled by adjusting nut 21. This essentially sets the position at which the diamond wedge is held at the rest or loading position. This is nominally 0.002 inches from the blade edge.

Spring means in the form of paired coil springs 22 extend between rod 20 and housing 37. The spring resists the force applied by said second voice coil. The current then effectively controls the displacement of the coil. If the current is varied with time, the displacement varies with time. Since displacement in time is velocity; the coil current therefore controls velocity. The second coil, second magnet, spring means and time-varying current through the coil constitute a velocity control.

Electronic circuitry 34 serves as means for supplying time-variable polarized D.C. current independently to said first and second coils. The timing of D.C. Current is controlled by a computer 35 interactive through leads 36 communicating between said computer and circuitry 34.

A diamond indenter in the form of wedge 23 is orthogonally emergent from rear surface 14 of second extremity portion 12. The wedge is positioned so as to impinge upon a blade specimen 24 whose edge 25 is to be measured for sharpness.

Holding means 27, separately mounted from the rocker arm, secures the blade specimen and adjustably positions it for proper contact by the diamond wedge. A displacement transducer 28 is associated with rear surface 14 of second extremity 12. The preferred displacement measuring device is a Linear Variable Displacement Transformer, consisting of a movable core 30 attached to the rocker arm, and a fixed assembly of transformer windings 31 surrounding the core. When the primary winding is excited by an alternating current, the summed voltage output of the two secondary windings varies as the position of the core is varied. Lead wires 32 route the electrical output of transducer 28 to computer 35.

In the operation of the device, a blade to be tested is properly positioned before the diamond wedge, whose edge is perpendicular to the edge of the test blade and about 0.002" to 0.005 before the edge. The current supplied to coil 16 is held to a constant level of about 3 milliamps prior to the operating cycle of the device. This constant level corresponds to the minor force on the diamond of a fraction of a gram. This force does not result in any displacement of the diamond towards the edge because it is restrained by a constant current on the coil 18 of about 20 milliamps.

At the initiation of the starting switch, the current through coil 18 is reduced to zero with time and then goes negative to about minus 20 milliamps. This causes the position of the diamond to proceed at a nearly constant velocity of about 0.002" per second until is reaches the blade edge. At that point the engaging nut 21 no longer holds back the rocker arm but proceeds by it. While the diamond is contacting the blade edge with this minor force, a reading of position is recorded from displacement gauge 28. The current on coil 16 is then increased to about 50 milliamps, which causes a force of about 20 grams to be exerted on the diamond. This force is held for a few seconds until the flow of edge material is complete, and then the current level is reduced back to the original value, 3 milliamps. While the force has been reduced the diamond remains fixed, within the edge crater made by the larger force. Now another reading of displacement gauge 28 is made and recorded. The current through coil 18 is now restored to its initial value of 20 milliamps. This current now withdraws the diamond to its original position off the blade edge, thereby completing the measurement cycle. The difference of the two readings recorded by displacement gauge 28 is an accurate representation of the extent of diamond displacement into the edge.

Computer 35, while not an essential component of the apparatus of this invention, is preferably utilized to control timing of sequences and provide a video display of the output of transducer 28. Timing tells the device when to start, when to take a reading of (i.e. remember) the position of the Diamond wedge contacting the edge at minimal force, when to increase the force to the higher level, how long the Diamond wedge should dwell on the edge, when to reduce the force, when to take the reading of the final position of the Diamond on the edge and then when to withdraw.

The LVDT is essentially an Analog device. While it is possible to remember and arithmetically process analog signals it is much easier and more accurate to use Digital. A computer is a convenient tool for this conversion and Arithmetic. The LVDT puts out signals in the millivolt range, by use of electronic amplification, one millivolt corresponds to 0.001 inches. The differential reading on the blade edge falls in the 50 to 100 microinch range, about 1.25 to 2.5 microns.

The Computer (PC), since it uses a Video display, can be used in place of an oscilloscope in showing the time dependent functions such as the coil currents and the instantaneous displacement of the Diamond. It can also do the Arithmetic and display the digital values of the differential displacement and process them for statistical significance.

Interpretation of the instrument values in terms of good and bad can only be done by relating them to shaver testing. In general, blades with an indent value >90 microinches represents a weak blade, while <60 microinches represents a strong but dull blade. Shaver preference is involved in describing them as "good" or "bad".

To utilize the device of this invention for testing the hardness of surfaces the 170 degree diamond wedge is replaced with a 136 degree diamond pyramid. By employing appropriate voice coil currents and attendant force levels, the hardness of a surface may be measured at various depths. This applies particularly to measuring case hardness depths, which now can only be determined by metallurgical sectioning, as in characterizing carburized steel.

The device of this invention may be utilized either as a laboratory tool or as a production monitoring and control device.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A device for testing a specimen so as to measure the strength of a cutting edge of a blade or the hardness of a surface, said device comprising:

a) a rigid housing, b) an elongated rocker arm extending to first and second extremities, each extremity having opposed front and rear surfaces, said rocker arm supported at its midpoint by pivot means held by said housing, c) a first coil of electrical wire mounted upon said front surface adjacent said first extremity and interactively associated with a stationary first magnet mounted on said housing, whereby a D.C. electrical current fed to said first coil causes said first coil to move toward said first magnet, thereby imparting torque to said rocker arm, d) a second coil of electrical wire interactively associated with a stationary second magnet mounted on said housing whereby a D.C. electrical current fed to said second coil causes said second coil to move toward said second magnet, thereby imparting torque to said rocker arm in a direction opposite to the torque produced at said first extremity, said second coil being affixed to a rod slidably penetrating said rocker arm adjacent the second extremity thereof, said rod being attached by spring means to said housing, e) a diamond indenter orthogonally emergent from the rear surface of said second extremity and positioned to impinge upon a specimen to be tested, f) holding means for adjustably securing said specimen in operative juxtaposition with said indenter, g) means for supplying time variable D.C. current independently to said coils, and h) measuring means which produce an electrical output signal corresponding to the distance of movement of said indenter.

2. The device of claim 1 wherein said indenter is a wedge and said specimen is the cutting edge of a blade.

3. The device of claim 2 wherein said wedge has an angle of about 170 degrees.

4. The device of claim 1 wherein said measuring means is a linear variable differential transformer displacement gauge having an inner core attached to said rocker arm and a stationary outer core supported by said housing.

5. The device of claim 1 wherein said rod is threaded and provided with a motion-limiting nut which restrains motion of the rocker arm in one polarity and releases said arm when the current is reversed.

6. The device of claim 1 further including a computer electronically interactive between said measuring means and means for supplying time variable D.C. current.

7. The device of claim 1 wherein said indenter is of 136 degree pyramidal contour.

* * * * *